United States Patent [19]
Greenberg

[11] Patent Number: 5,977,166
[45] Date of Patent: Nov. 2, 1999

[54] ENHANCED FLAVORS USING MENTHONE KETALS

[75] Inventor: Michael J. Greenberg, Northbrook, Ill.

[73] Assignee: WM. Wrigley Jr. Company, Chicago, Ill.

[21] Appl. No.: 08/036,473

[22] Filed: Mar. 24, 1993

Related U.S. Application Data

[62] Division of application No. 07/845,344, Mar. 4, 1992, abandoned, which is a continuation of application No. 07/609,879, Nov. 6, 1990, abandoned.

[51] Int. Cl.$^6$ ............... A23G 3/30; A61K 9/68; A61K 7/16; A61K 31/335
[52] U.S. Cl. ............... 514/452; 424/48; 424/49; 426/3; 514/450; 514/462; 514/467; 514/901
[58] Field of Search .................. 426/3–6, 536, 426/538, 651; 424/48, 49; 514/450, 452, 462, 467, 901

[56] References Cited

U.S. PATENT DOCUMENTS

| | | | |
|---|---|---|---|
| 3,096,345 | 7/1963 | Hechenbleikner et al. | 260/340.7 |
| 3,206,474 | 9/1965 | Hechenbleikner et al. | 260/340.7 |
| 3,257,480 | 6/1966 | Hechenbleikner et al. | 260/937 |
| 3,349,150 | 10/1967 | Hechenbleikner et al. | 260/929 |
| 3,737,463 | 6/1973 | Howard et al. | |
| 3,818,107 | 6/1974 | Yolles | 426/3 |
| 3,830,930 | 8/1974 | Moeller et al. | 424/308 |
| 3,857,964 | 12/1974 | Yolles | 426/3 |
| 3,917,613 | 11/1975 | Humbert et al. | 260/293.65 |
| 3,991,178 | 11/1976 | Humbert et al. | 424/54 |
| 4,032,661 | 6/1977 | Rowsell et al. | 424/337 |
| 4,033,994 | 7/1977 | Watson et al. | 260/468 R |
| 4,059,118 | 11/1977 | Watson et al. | 131/8 R |
| 4,070,449 | 1/1978 | Rowsell et al. | 424/45 |
| 4,070,496 | 1/1978 | Rowsell et al. | 424/45 |
| 4,136,163 | 1/1979 | Watson et al. | 424/54 |
| 4,150,052 | 4/1979 | Watson et al. | 260/557 R |
| 4,153,679 | 5/1979 | Rowsell et al. | 424/45 |
| 4,157,384 | 6/1979 | Watson et al. | 424/45 |
| 4,178,459 | 12/1979 | Watson et al. | 560/125 |
| 4,190,643 | 2/1980 | Watson et al. | 424/54 |
| 4,193,936 | 3/1980 | Watson et al. | 260/557 R |
| 4,206,301 | 6/1980 | Yolles | 426/3 |
| 4,226,988 | 10/1980 | Watson et al. | 544/176 |
| 4,230,688 | 10/1980 | Rowsell et al. | 424/45 |
| 4,296,093 | 10/1981 | Rowsell et al. | 424/45 |
| 4,296,137 | 10/1981 | Boden | 426/534 |
| 4,296,138 | 10/1981 | Boden | 426/534 |
| 4,296,255 | 10/1981 | Roswell et al. | 564/215 |
| 4,330,417 | 5/1982 | Boden | 252/8.9 |
| 4,339,341 | 7/1982 | Boden | 252/174.11 |
| 4,341,646 | 7/1982 | Boden | 252/8.9 |
| 4,347,857 | 9/1982 | Boden | 131/276 |
| 4,348,416 | 9/1982 | Boden | 426/3 |
| 4,357,315 | 11/1982 | Boden | 424/49 |
| 4,387,036 | 6/1983 | Boden | 252/174.11 |
| 4,405,510 | 9/1983 | Boden | 252/522 R |
| 4,419,280 | 12/1983 | Boden | 252/522 R |
| 4,421,125 | 12/1983 | Boden | 131/276 |
| 4,459,425 | 7/1984 | Amano et al. | 568/666 |
| 4,780,324 | 10/1988 | Knebl et al. | 426/3 |
| 5,266,592 | 11/1993 | Grub et al. | 424/48 |
| 5,348,750 | 9/1994 | Greenberg | 426/3 |

FOREIGN PATENT DOCUMENTS

| | | |
|---|---|---|
| 0048545A3 | 3/1982 | European Pat. Off. . |
| 0080148A1 | 6/1983 | European Pat. Off. . |
| 0297048A3 | 12/1988 | European Pat. Off. . |
| 0485170A1 | 5/1992 | European Pat. Off. . |
| 0-507190 | 10/1992 | European Pat. Off. . |
| 2022369 | 11/1971 | Germany . |
| 2339661 | 2/1974 | Germany . |
| 2433165 | 1/1975 | Germany . |
| 2608226 | 8/1977 | Germany . |
| 445832 | 7/1968 | Switzerland . |
| 1422998 | 1/1976 | United Kingdom . |

OTHER PUBLICATIONS

V. Boekelheide et al., *J. Amer. Chem. Soc.,* 71(10), 3303–7(Oct. 20, 1949), "Drugs effecting muscular paralysis. Some substituted dioxolanes and related compounds."

A.A. Svishchuk et al., *N.Kh. Ukr. Khim. Zh.* (*Russ. ed.*), 43(2), 173–76 (1977 (with translation).

G. Taillandier et al., *Il Farmaco, Edizione Scientifica,* 35(2), 89–109 (Feb. 1980) (no translation presently available).

Arctander, "Perfume and Flavor Chemicals (Aroma Chemicals)," privately published Montclair, N.J., 1969.

Svishchuk et al., "Chemical Reactions of d,1–Menthone," *Ukranian Chemical Journal,* No. 2, 1977, pp. 173–176 (translation provided).

*Primary Examiner*—Arthur L. Corbin
*Attorney, Agent, or Firm*—Brinks Hofer Gilson & Lione

[57] ABSTRACT

A method is disclosed for enhancing flavors in low moisture consumable items, including chewing gum, using menthone ketals. Chewing gum, oral compositions, pharmaceuticals, and low moisture foods containing menthone ketals are provided.

23 Claims, 9 Drawing Sheets

ENHANCED FLAVORS USING MENTHONE KETALS

CROSS-REFERENCE TO RELATED APPLICATIONS

This is a division of application Ser. No. 07/845,344, filed Mar. 4, 1992, and now abandoned, which is a continuation of application Ser. No. 07/609,879, filed Nov. 6, 1990, and now abandoned.

BACKGROUND OF THE INVENTION

The present invention relates to the use of menthone ketal compounds as flavor ingredients. More particularly, the present invention relates to the use of menthone ketals to enhance flavors in chewing gum and other low moisture consumable items.

Efforts have been undertaken to improve and optimize flavor attributes of consumable items, including chewing gum. Difficulties often arise when altering ingredients in such items. Implementing ingredient changes, even those that involve small amounts of flavor ingredients, may cause variation in other characteristics of the composition. These characteristics include texture, sweetness, processability, and flavor-release attributes.

The aforementioned difficulties are especially true in chewing gum compositions which are complex systems, containing a gum base, bulking and sweetening ingredients, plasticizers, colors, fillers and many other ingredients. Reformulation of these compositions is very costly and time consuming.

SUMMARY OF THE INVENTION

In accordance with one embodiment of the present invention, menthone ketals are used as flavor ingredients. One compound disclosed herein, menthone-glycerol ketal, enhances and modifies flavors, particularly mint flavors, and provides a refreshing and cooling taste to the consumer. Another compound disclosed herein, menthone-propylene glycol ketal, provides sweet minty, eucalyptus and licorice notes as well as enhances and modifies mint and other flavors. This compound further provides a cooling effect, although less intensive than menthone-glycerol ketal. Such attributes are useful in chewing gum, pharmaceuticals, and other low moisture foods and oral compositions such as toothpaste and mouthwash.

Another embodiment of the present invention is a method of preparing chewing gum arid other low moisture consumable items which includes adding menthone ketal to enhance and modify flavors.

A further embodiment of the present invention is a chewing gum composition which includes gum base, softener, sweetener, and menthone ketal as a flavor ingredient.

The present invention is also an oral composition, pharmaceutical, or low moisture food which includes menthone ketal as a flavor ingredient.

The present invention provides a relatively simple and inexpensive method for enhancing and modifying flavors. In particular, the present invention can be carried out in a short time, using simple and inexpensive equipment. The present invention is also well suited for batch processing.

The phrase "menthone ketal," as used herein, contemplates all compounds formed in the chemical reaction of menthone with alcohols containing 1 to 8 carbons or polyols containing 2 to 8 carbons and all structural and optical isomers thereof. It should be further noted that the phrases "menthone-glycerol ketal" and "menthone-propylene glycol ketal" as used in this application refer to all structural and optical isomers of these respective compounds.

DETAILED DESCRIPTION OF THE PREFERRED EMBODIMENTS

Figure 1:
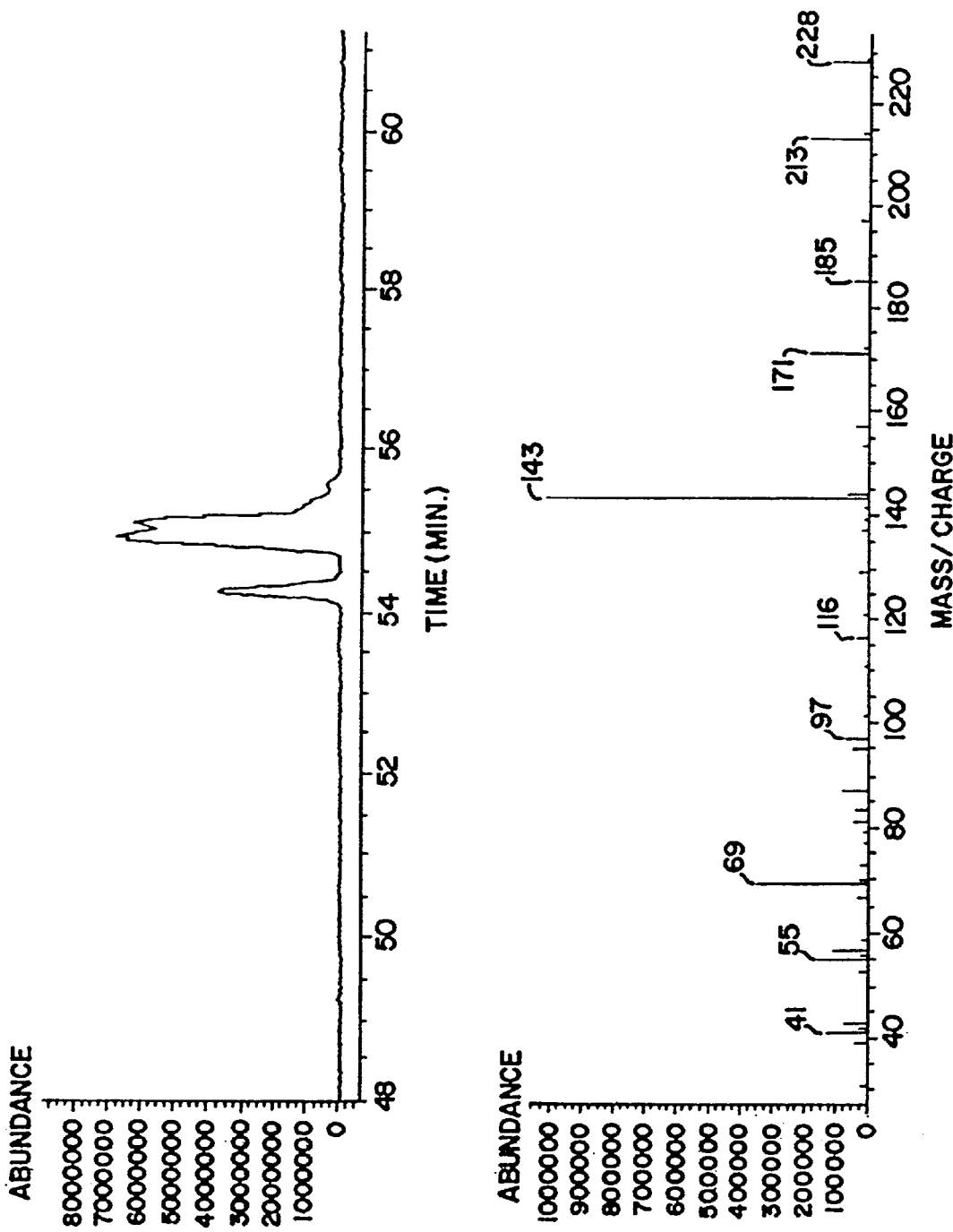
FIG. 1 shows the results of mass spectroscopy of menthone-glycerol ketal, the structural isomer designated "I" herein.

Ketals are typically produced by the chemical reaction of a ketone with an alcohol. Cyclic ketals are formed when the ketone is reacted with a di- (or higher) functional alcohol, ie. an alcohol containing 2 or more hydroxy groups.

The present invention contemplates the use of menthone ketals which can be produced by reacting menthone with an alcohol containing 1 to 8 carbons or a polyol containing 2 to 8 carbons to form a compound of formulae:

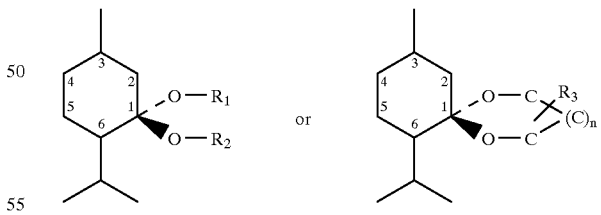

wherein $R_1$ and $R_2$ are alkyl groups; $R_3$ is a hydroxy, lower alkoxy, or lower alkyl group; and n is an integer of 0 or 1.

Two cyclic menthone ketals, menthone-glycerol ketal and menthone-propylene glycol ketal, are particularly useful as flavorings. Both are not known to occur in nature, and both have isomers.

Menthone-glycerol ketal is formed in the chemical reaction of menthone with glycerol. This reaction produces three structural isomers (designated I, II, and III below) having the following structures:

I.

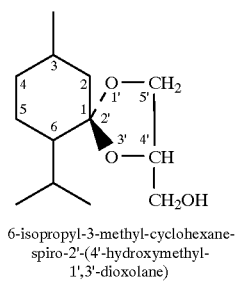

6-isopropyl-3-methyl-cyclohexane-
spiro-2'-(4'-hydroxymethyl-
1',3'-dioxolane)

II.

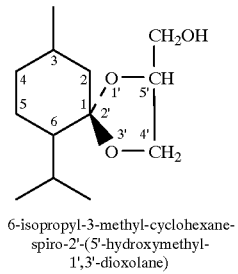

6-isopropyl-3-methyl-cyclohexane-
spiro-2'-(5'-hydroxymethyl-
1',3'-dioxolane)

III.

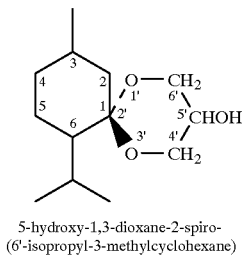

5-hydroxy-1,3-dioxane-2-spiro-
(6'-isopropyl-3-methylcyclohexane)

In structures I and II, carbons 1, 3, 6, and 4' (structure I) or 5' (structure II) are chiral centers. C(arbons 3 and 6 have a predetermined configuration when the starting material is optically pure 1-menthone. However, impurities such as d-menthone and isomenthone which have different configurations of the 3 and 6 carbons are likely to be present in the starting material.

The configuration of carbon 1, which is fixed during the reaction, determines which positional structural isomer will be formed when the product is a dioxalane (structures I and II), but is not chiral in the dioxane isomer (structure III). The configuration of the remaining chiral center (carbons 4' or 5') is also fixed during the reaction and results in two optical isomers of each structural isomer, resulting in six distinct products. Where the starting material is a racemic mixture of d- and 1-menthone and isomenthone (ie. four different isomers), the product will contain 24 different isomers.

Menthone-glycerol ketal is synthesized according to the method described in Example 1 and then analyzed. A variety of known methods may be used to determine identity, including capillary gas chromatography, gas chromatography/mass spectroscopy, and infrared spectroscopy. Capillary gas liquid chromatography analysis indicated that the menthone-glycerol ketal produced was 93% pure with an overall yield of 44% (40 g).

Figure 2:
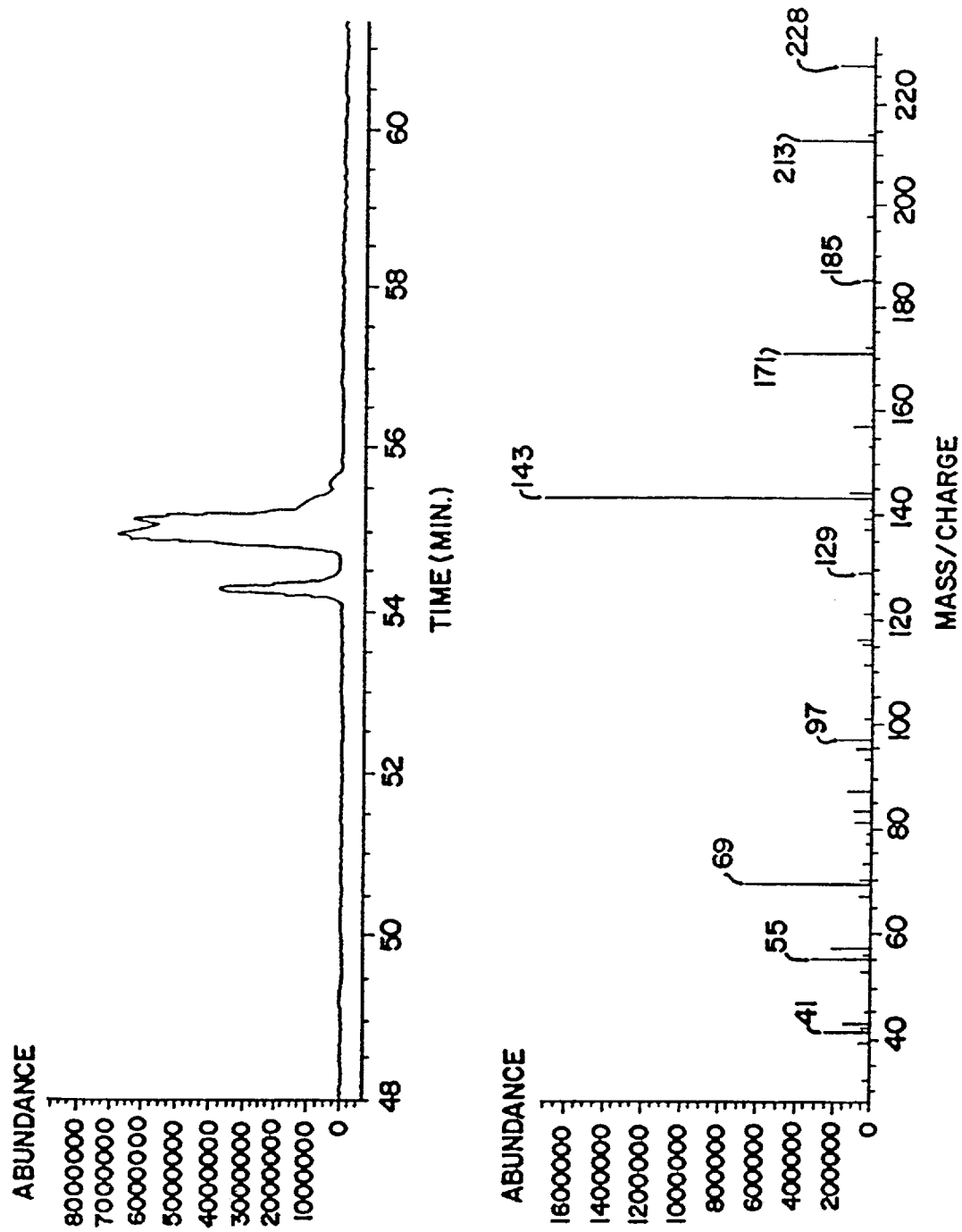
FIG. 2 shows the results of mass spectroscopy of menthone-glycerol ketal, the structural isomer designated "II" herein.
Figure 3:
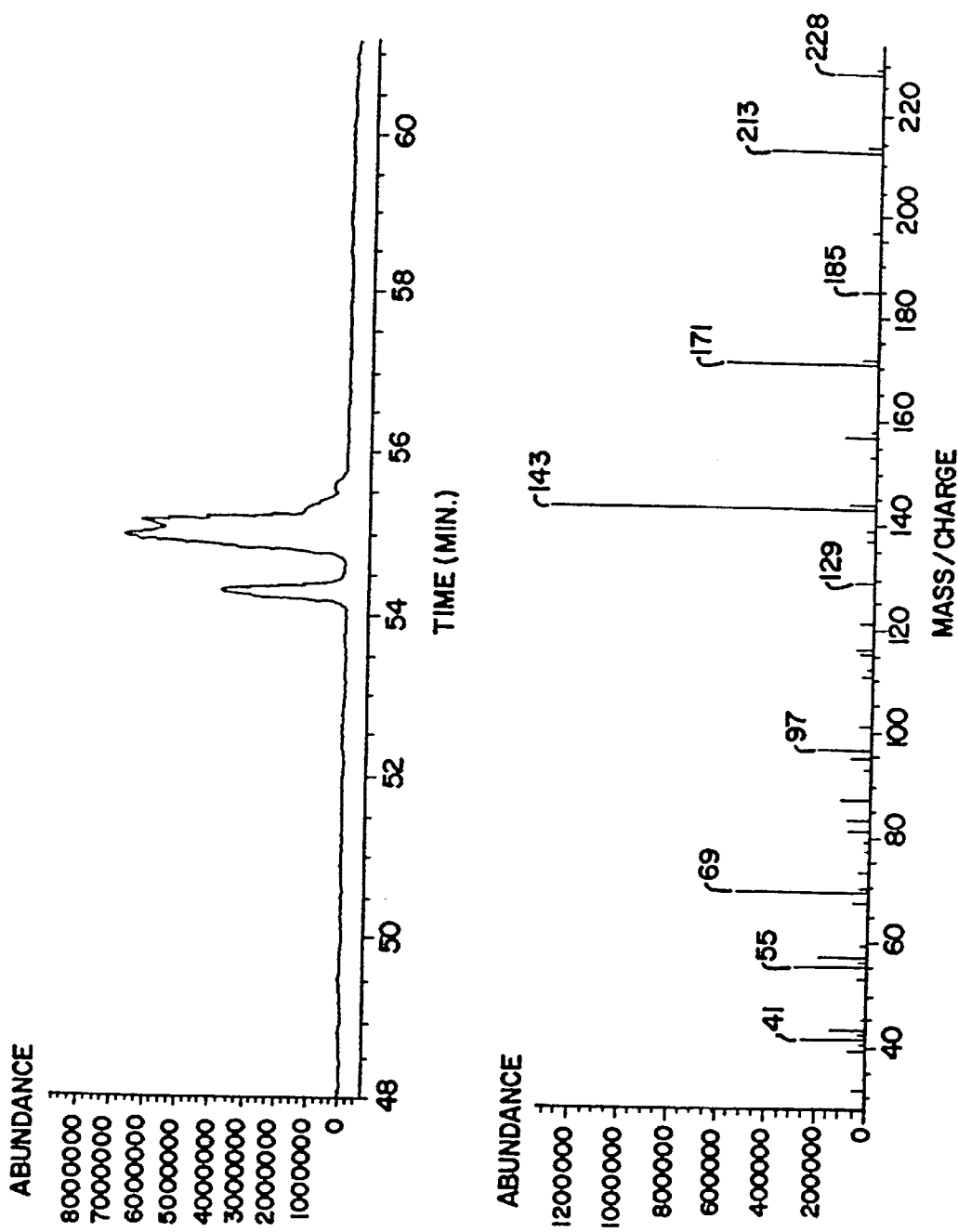
FIG. 3 shows the results of mass spectroscopy of menthone-glycerol ketal, the structural isomer designated "III" herein.
Figure 4:
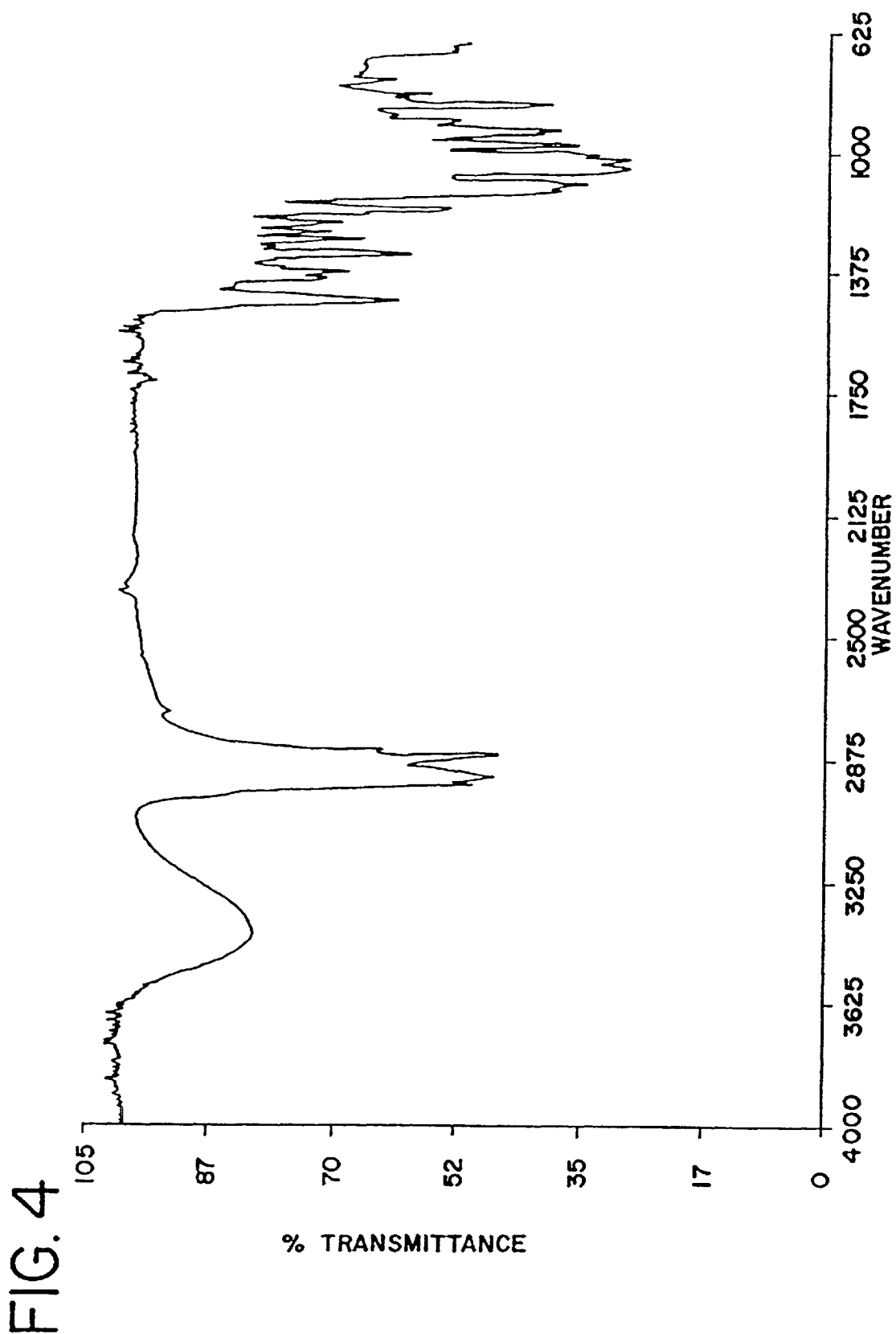
FIG. 4 shows the results of infrared spectroscopy of menthone-glycerol ketal.
Figure 5:
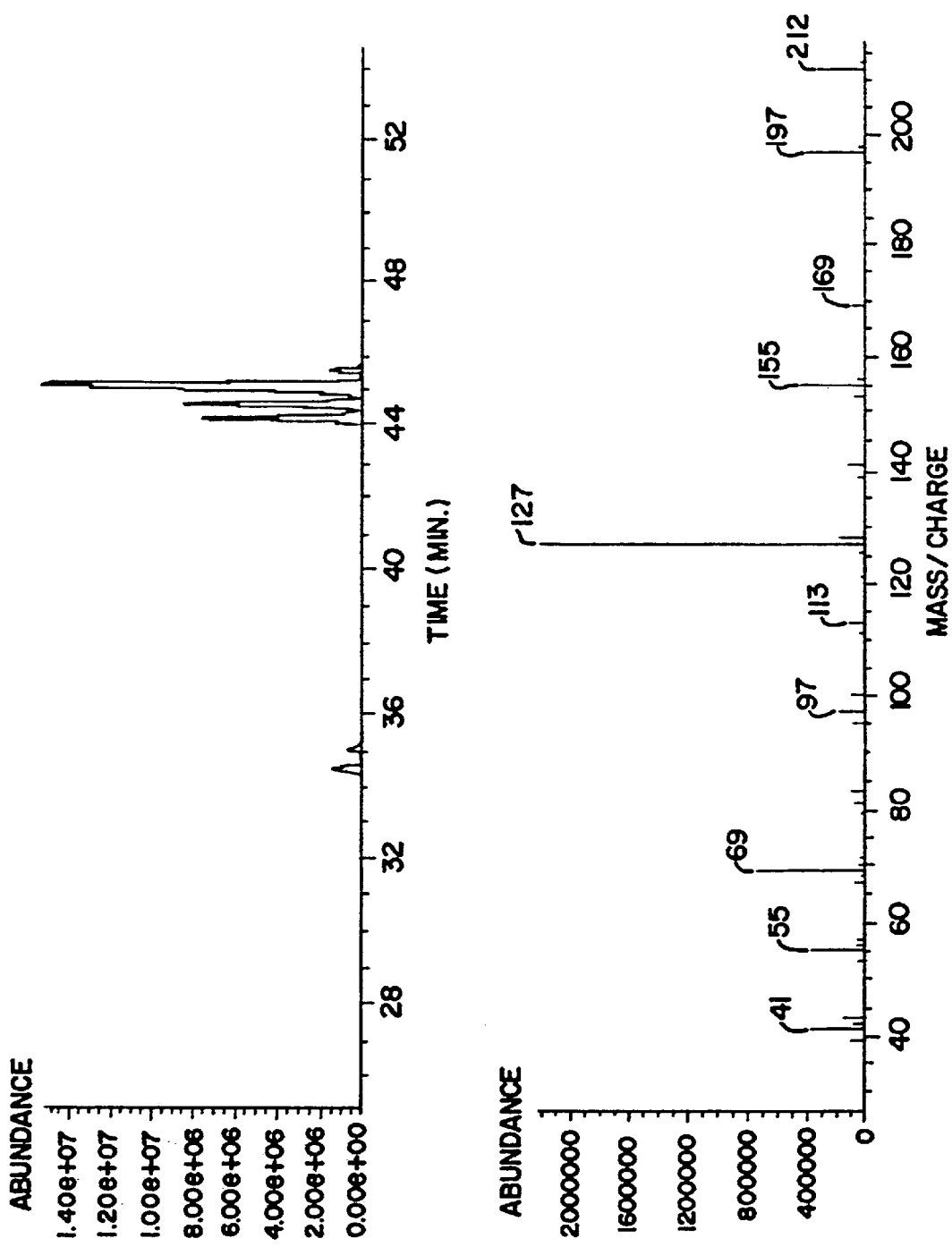
FIG. 5 shows the results of mass spectroscopy of an isomer of menthone-propylene glycol ketal at Peak 1.
Figure 6:
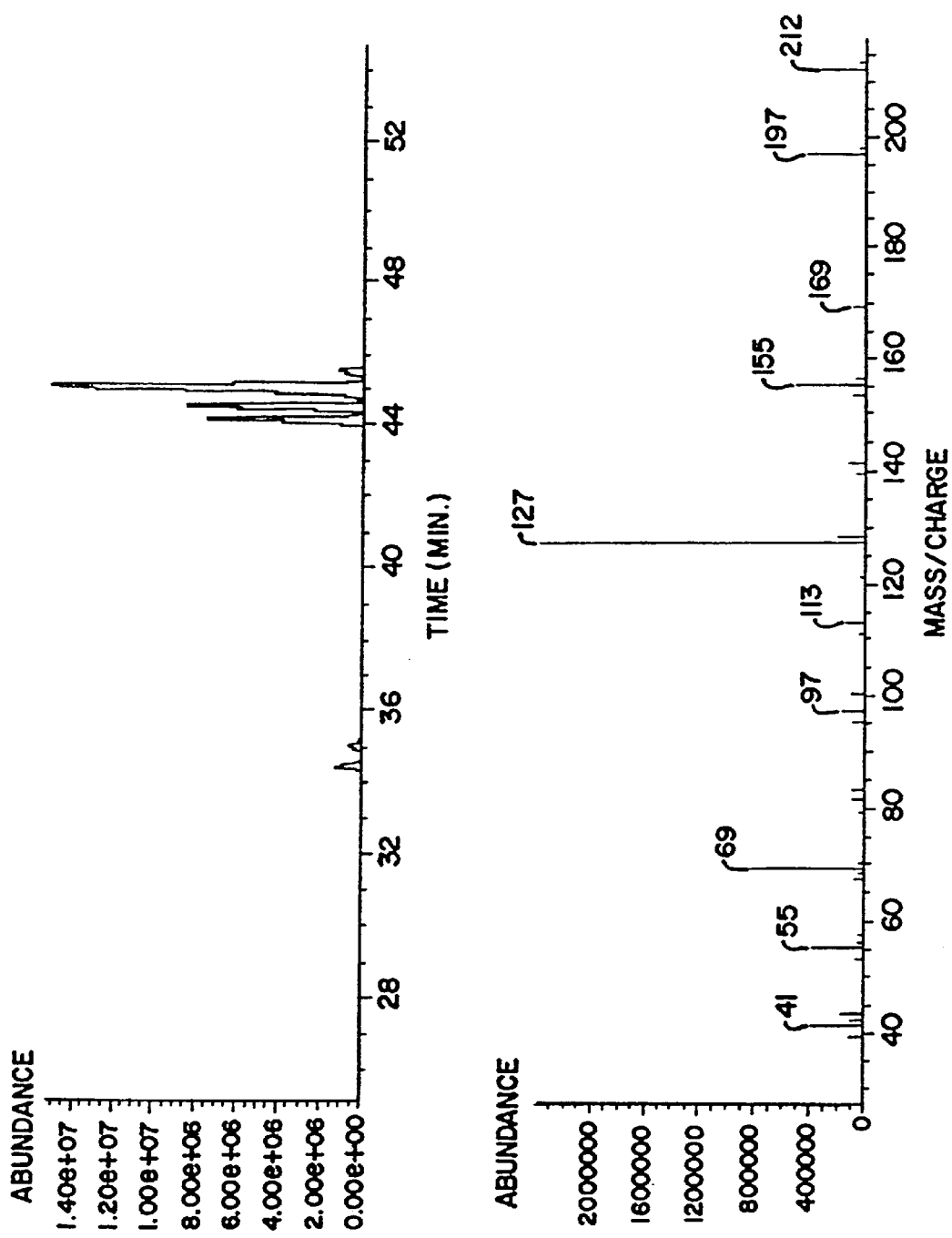
FIG. 6 shows the results of mass spectroscopy of an isomer of menthone-propylene glycol ketal at Peak 2.
Figure 7:
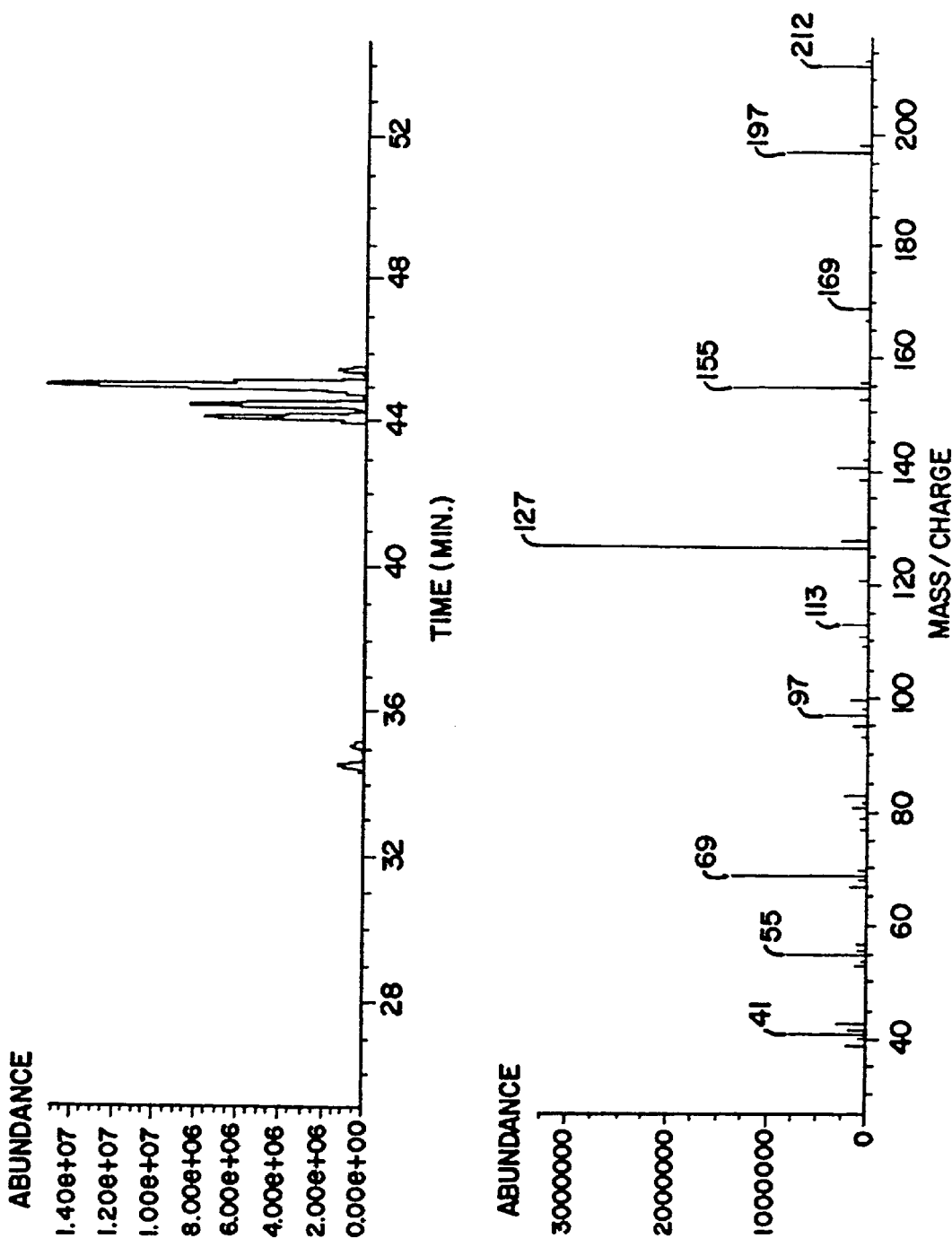
FIG. 7 shows the results of mass spectroscopy of an isomer of menthone-propylene glycol ketal at Peak 3.
Figure 8:
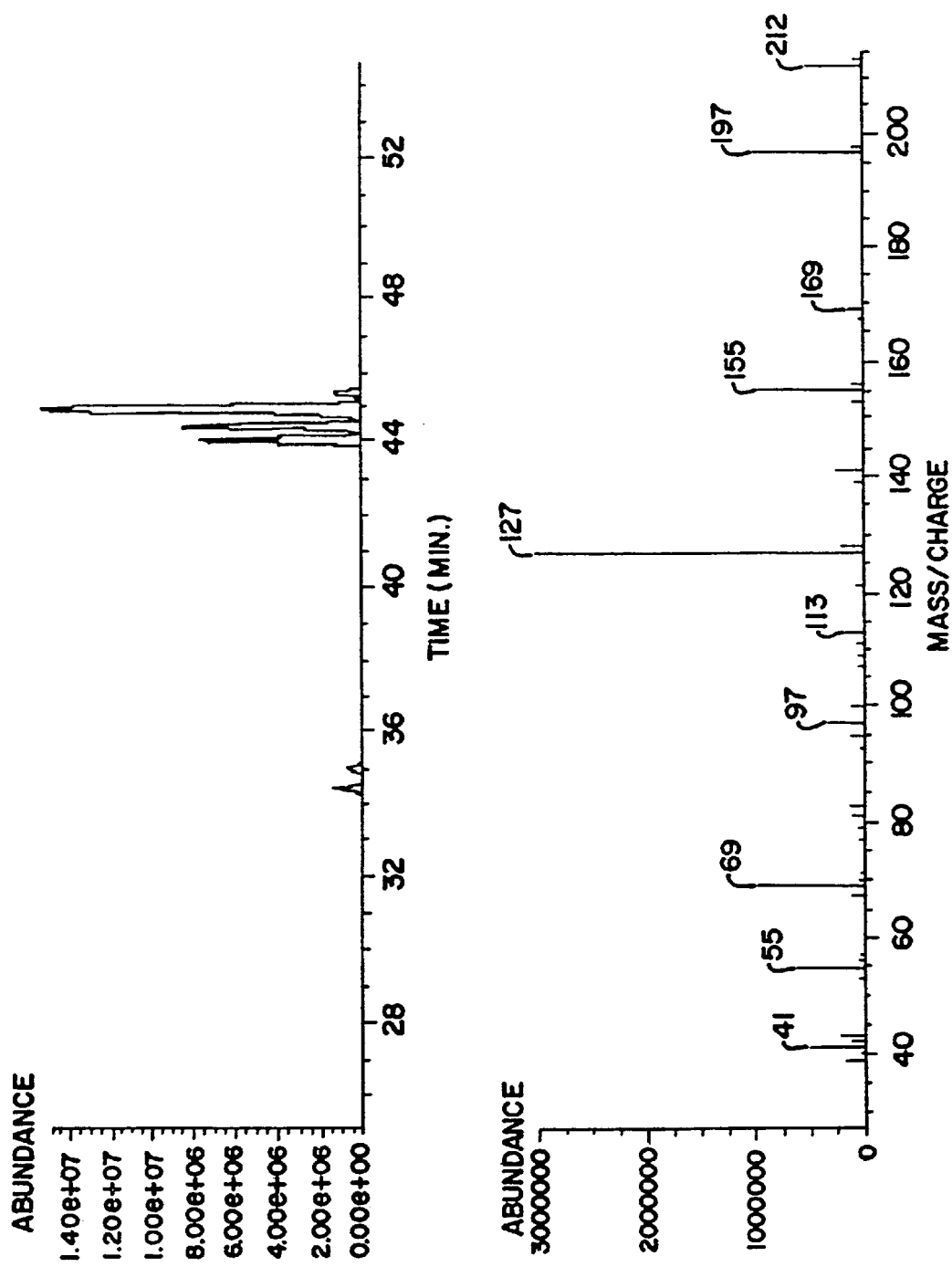
FIG. 8 shows the results of mass spectroscopy of an isomer of menthone-propylene glycol ketal at Peak 4.

The results of mass spectroscopy for the menthone-glycerol ketal produced in Example 1 are shown in FIGS. 1, 2, and 3. As these figures demonstrate, all three structural isomers (designated I–III above) have the same mass spectral profile. These mass spectral profiles confirm the expected molecular weight of menthone-glycerol ketal to be 228 g/mol. The results of infrared spectroscopy are shown in FIG. 4. The peaks at 1039.13cm$^{-1}$ and 1094.36 cm$^{-1}$ are characteristic of C—O—C—O—C absorption of ketals. The broad peak at about 3400 cm$^{-1}$ is due to O—H stretching. The fairly strong peak at 1109.23 cm$^{-1}$ could be C—O stretching of a secondary alcohol.

Another cyclic menthone ketal, menthone-propylene glycol ketal, is formed by the chemical reaction of menthone with 1,2-propylene glycol. The menthone-propylene glycol ketal produced has two positional structural isomers (designated I and II below) having the following structures:

I.

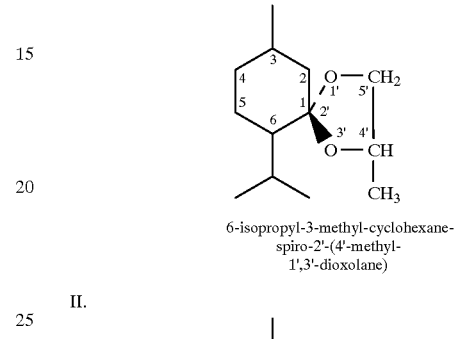

6-isopropyl-3-methyl-cyclohexane-
spiro-2'-(4'-methyl-
1',3'-dioxolane)

II.

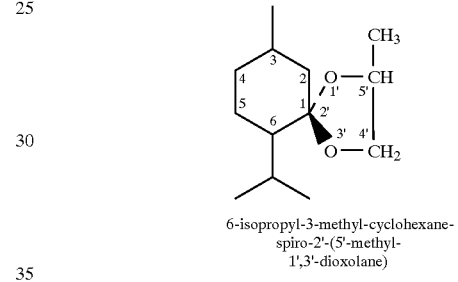

6-isopropyl-3-methyl-cyclohexane-
spiro-2'-(5'-methyl-
1',3'-dioxolane)

Carbons 1, 3, 6, and 4 (structure I) or 5 (structure II) in structures I and II are chiral centers. Carbons 3 and 6 have a predetermined configuration when the starting material is optically pure 1-menthone. However, impurities such as d-menthone and isomenthone which have different configuration of the 3 and 6 carbons are likely to be present in the starting material.

The configuration of carbon 1, which is fixed during the reaction, determines which positional structural isomer will be formed. The configuration of the remaining chiral center (carbons 4 or 5) is also fixed during the reaction and results in two optical isomers of each structural isomer, resulting in four distinct products. Where the starting material is a racemic mixture of d- and 1-menthone and isomenthone (ie. four different isomers), the product will contain 16 different isomers.

Menthone-propylene glycol ketal is synthesized according to the method described in Example 4 and then analyzed. Capillary gas liquid chromatography analysis indicated that the menthone-propylene glycol ketal produced was 95% pure with an overall yield of 83% (70 g).

Figure 9:
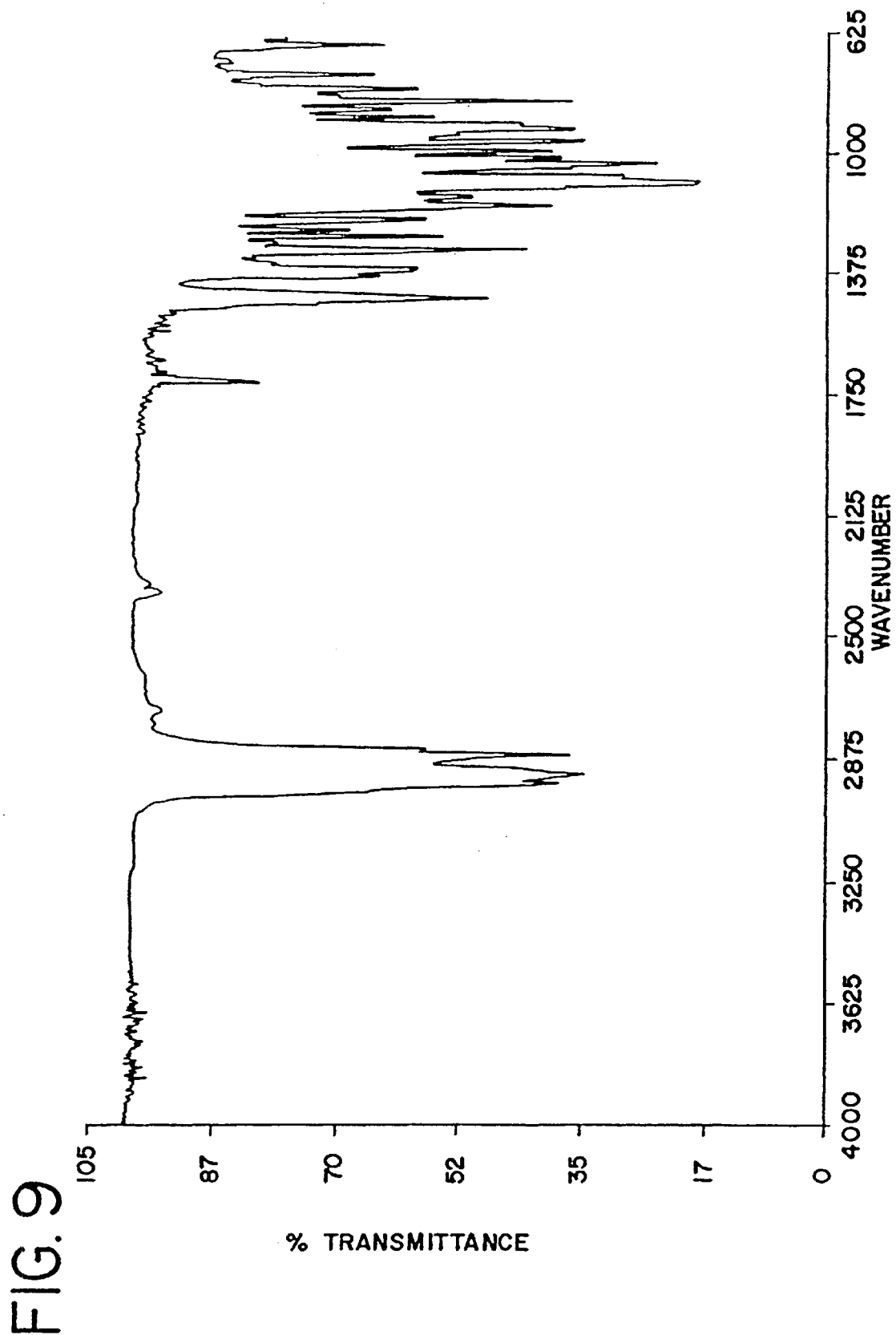
FIG. 9 shows the results of infrared spectroscopy of menthone-propylene glycol ketal.

The results of mass spectroscopy for the menthone-propylene glycol ketal produced in Example 4 are shown in FIGS. 5, 6, 7 and 8. As these figures demonstrate, four isomers were present having the same mass spectral profile. These mass spectral profiles confirm the ketal structure and expected molecular weight of menthone-propylene glycol ketal to be 212 g/mol. The results of infrared spectroscopy are shown in FIG. 9. The peaks at 1041.4 cm$^{-1}$, 1079 cm$^{-1}$, .95 cm, 1137.995 cm$^{-1}$ and 1163.7 cm$^{-1}$ are characteristic of C—C—C—O—C absorption for ketals. No alcohol peaks are apparent. The fairly weak peak at 1713.3 cm$^{-1}$ due to C—O stretching is a result of trace amounts of menthone (about 5%) in the sample.

The present invention contemplates the blending of menthone ketals with many flavor ingredients, including but not limited to, citrus oils, fruit essences, and spice blends, both natural and synthetic. Those skilled in the art will recognize that natural and artificial flavor ingredients may be combined with menthone ketals in any manner. More particularly, the present invention contemplates the blending of menthone ketals with mint flavors, including peppermint oil, spearmint oil, and oil of wintergreen. All such flavor ingredients and blends are contemplated for use in the present invention.

In a presently preferred embodiment, such flavor mixtures are added to chewing gum. Flavor ingredients in chewing gum comprise about 0.25% to about 5% by weight of gum. When used in chewing gum, optimum levels of menthone ketals are preferably determined by sensory testing. The amount of any given menthone ketal added may vary from about 0.001% to about 1%. Preferably, the level of menthone ketals is about 0.1% to about 50% of the total flavor added.

In general, a chewing gum comprises a water-soluble bulk portion, a water-insoluble chewable gum base portion and typically, water-insoluble flavor ingredients. The water-soluble bulk portion dissipates with a portion of the flavor over time during chewing. The gum base portion is retained in the mouth throughout the chew.

The insoluble gum base generally comprises elastomers, resins, fats and oils, waxes, softeners and inorganic fillers. The insoluble gum base constitutes between about 5% to about 95% of the gum, and more preferably about 20% to 30%. All percent values represent weight percent.

The gum base typically also includes a filler component. The filler component may be calcium carbonate, magnesium carbonate, talc, dicalcium phosphate; and the like. The filler may constitute between about 5% to about 60% of the gum base. Preferably, the filler comprises about 5% to 50% of the chewing gum base. The gum base also contains softeners, including glycerol monostearate and glycerol triacetate. Further, gum bases may also contain additional ingredients such as antioxidants, colors, and emulsifiers. The present invention contemplates using any commercially acceptable gum base.

The water-soluble portion of chewing gum may further comprise softeners, sweeteners, and flavors and combinations thereof. The softeners are added to the chewing gum to optimize the chewing ability and mouth feel of the gum. Softeners, also known in the art as plasticizers, generally constitute about 0.1% to about 15% of the chewing gum. Softeners contemplated by the present invention include glycerin, lecithin and combinations thereof. Aqueous sweetener solutions such as those containing sorbitol, hydrogenated starch hydrolysates, corn syrup, and combinations thereof may be used as softeners and binding agents in gum.

Sweeteners contemplated by the present invention for use in chewing gum include both sugar and sugarless components. Sugar sweeteners generally include saccharide-containing components commonly known in the art and include, but are not limited to, sucrose, dextrose, maltose, dextrin, dried invert sugar, fructose, levulose, galactose, corn syrup solids and the like, alone or in any combination. Sugarless sweeteners include components with sweetening characteristics but are devoid of the commonly known sugars and comprise, but are not limited to, sugar alcohols such as sorbitol, mannitol, xylitol, hydrogenated starch hydrolysates, maltitol, and the like, alone or in any combination. Also contemplated for direct addition to the gum are high intensity sweeteners such as aspartame, sucralose, cyclamate, acesulfame-K, dihydrochalones, glycyrrhizin, alitame, and saccharin, and the food acceptable salts thereof.

Those persons skilled in the art will recognize that any combination of sugar/sugarless sweeteners may be employed in the chewing gum. Further, those skilled in the art will recognize a sweetener may be present in a chewing gum in whole or in part as a water-soluble bulking agent, and that the softener may be combined with a sweetener such as an aqueous sweetener solution.

In general, chewing gum is manufactured by sequentially adding the various chewing gum ingredients to any commercially available mixer known in the art. After the ingredients have been thoroughly mixed, the gum mass is discharged from the mixer and shaped into the desired forms such as by rolling into sheets and cutting into sticks, extruding into chunks, or casting into pellets. Generally, the ingredients are mixed by first melting the gum base and adding it to the running mixer. The base may also be melted in the mixer itself. Color may also be added at this time. A softener such as glycerin may then be added next along with the syrup and a portion of bulking agent. Further portions of the bulking agents may be added to the mixer. Preferably, the flavor ingredients are added to the gum mixture near the end of the mixing process. The entire mixing procedure takes from about 5 minutes to 15 minutes, however, longer mixing times may be required. Those persons skilled in the art will recognize that many variations of the above described procedure may be followed.

In another embodiment, menthone ketals may be used to flavor a variety of other products, including foodstuffs with a low moisture content, such as candies, dry beverage, gelatin, and pudding mixes, drugs, and other oral compositions such as toothpaste and mouthwash. Preferably, the formulation of the food is less than 2% by weight water. Preferably, the flavor comprises about 0.001% to about 2% of the oral composition.

Further details of the invention will become apparent from the following examples which, when taken into conjunction with the accompanying figures, disclose presently preferred embodiments of the present invention.

EXAMPLE 1

Synthesis of Menthone-Glycerol Ketal

Menthone-glycerol ketal is a clear, viscous liquid with a slight yellow tint. The observed boiling point is 135° C. at 2.0 mm Hg (approximately 295° C. at 760 mm Hg). The synthesis of menthone-glycerol ketal was performed as follows:

1. A 250 ml roundbottom flask was equipped with a stirring bar, Dean-Stark trap, and cold water condenser. A mixture comprising 30 g (0.2 mol) 95% 1-menthone, 20 g (0.22 mol) 98% glycerol, 2 g (0.01 mol) 99% p-toluene sulfonic acid, and approximately 100 ml HPLC grade toluene was added to the flask and placed on a stir plate.

2. The mixture was refluxed for 4–5 hours (approximately 3.4 ml of water collected). The mixture was then cooled to room temperature, transferred to a separatory funnel, and extracted twice with 50 ml of 0. 1M sodium hydroxide. At this stage, the excess catalyst, p-toluene sulfonic acid, was removed.

3. The aqueous layer was then decanted from the organic layer and discarded. The excess toluene was boiled off using a rotary evaporator (ROTOVAC). The above steps were repeated and the oils combined. Finally, the oil was dried with anhydrous sodium sulfate and distilled in-vacuo. The fraction at 2.0 mm Hg and 135–140° C. was collected.

4. A sample of the ketal was analyzed by capillary gas chromatography. Identification was confirmed by gas chromatography/mass spectroscopy and FT-IR. Approximately 40 g of the ketal was recovered with 93% purity.

EXAMPLE 2

Sensory Evaluation of Menthone-Glycerol Ketal Flavored Solution

The flavor of menthone-glycerol ketal was evaluated by sensory testing. A solution was prepared dissolving 0.1 ml of the described ketal in 10 ml of ethanol. Next, 1 ml of this mixture was added to 100 ml of 5% aqueous sucrose solution.

Five experienced flavor panelists evaluated the flavor of the solution by swishing 10ml in their mouths for 10 seconds, then expectorating the solution. All five panelists reported the cooling effect of the solution, with three of the five panelists making a second mention of the cooling property.

EXAMPLE 3

Sensory Evaluation of Chewing Gum Flavored with Menthone-Glycerol Ketal

Four laboratory-scale batches of gum were prepared and were chewed by experienced panelists. The batches of gum were prepared according to the following formula:

| Ingredient | % By Weight |
| --- | --- |
| Sugar | 54.451 |
| Base | 20.17 |
| Syrup | 13.32 |
| Glycerin | 1.29 |
| Dextrose | 9.89 |
| Flavor | 0.879 |
| | 100.000 |

The flavor used in the above formula was a peppermint oil. A fraction of the peppermint oil in the four different batches was replaced with 0, 5, 10, or 20% menthone-glycerol ketal. After blending and drying, the gum was cut into uniform pieces for testing.

The gums were evaluated by three trained panelists. While chewing each piece, each panelist recorded his or her sensations. The panelists reported that the 10% and 20% menthone-glycerol ketal gums had longer-lasting sweetness, creamy flavor similar to Doublemint® gum, and higher cooling effect.

EXAMPLE 4

Synthesis of Menthone-Propylene Glycol Ketal

Menthone-propylene glycol ketal is a colorless liquid with an observed boiling point at 72° C. at 0.6 mm Hg (approximately 245° C. at 760 mm Hg). The synthesis and analysis of menthone-propylene glycol ketal was performed as described in Example 1 except that 20 g (0.26 mol) 99+% 1,2-propylene glycol was added in Step 1 instead of 20 g glycerol. Also, in Step 3, the fraction at 0.6 mm–1.0 mm Hg and 71–73° C. was collected. Approximately 70 g of menthone-propylene glycol ketal was recovered with 95% purity. The structure was confirmed by GC-MS and FT-IR.

EXAMPLE 5

Sensory Evaluation of Menthone-Propylene Glycol Ketal Flavored Solution

The flavor of menthone-propylene glycol ketal was evaluated by trained panelists. First, 0.1 ml of the ketal was dissolved in 10 ml of ethanol. Next, 1 ml of the resulting solution was added to 100 ml of 5% aqueous sucrose solution.

Five experienced flavor panelists evaluated the flavor of the solution by swishing 10 ml in their mouths for 10 seconds, then expectorating the solution. Three of the five panelists reported eucalyptus and minty notes, while two of the five panelists reported both a licorice note and a sweet taste.

EXAMPLE 6

Sensory Evaluation of Chewing Gum Flavored with Menthone-Propylene Glycol Ketal

Four laboratory-scale batches of gum were prepared as described in Example 3 except that fractions of the peppermint oil was replaced with 0, 5, 10, or 20% menthone-prapylene glycol ketal.

The gums were evaluated by four trained panelists. While chewing each piece, each panelist recorded his or her sensations. Three panelists reported enhanced cooling effect and one panelist reported lingering sweetness even at five minutes. Another panelist noted a sweet creamy flavor.

In summary, a relatively simple and inexpensive method has been described for enhancing and modifying flavors in chewing gum, pharmaceuticals, and low moisture foods and oral products such as toothpaste and mouthwash, using menthone ketals. Although specific embodiments and examples have been described herein, it should be born in mind that these have been provided by way of explanation and illustration and that the present invention is not limited thereby. Modifications that are within the ordinary skill in the art to make are considered to lie within the scope of the invention as defined by the following claims, including all equivalents.

I claim:

1. A method of flavoring a low moisture oral composition which comprises adding flavor ingredients to a low moisture food or pharmaceutical composition so that flavor ingredients comprise about 0.001% to about 2% by weight of the composition, said flavor ingredients comprising a menthone ketal.

2. A method of preparing an oral composition having enhanced flavor which comprises adding flavor ingredients to an oral composition selected from the group consisting of food, pharmaceutical, toothpaste, and mouthwash so that flavor ingredients comprise about 0.001% to about 2% by weight of the composition, said flavor ingredients comprising a menthone ketal.

3. The method of claim 1 or 2, wherein said menthone ketal is a compound of the formula:

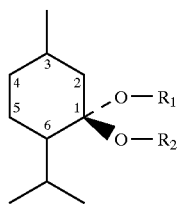

wherein $R_1$ and $R_2$ are alkyl groups.

4. The method of claim 1 or 2, wherein said menthone ketal is a compound of the formula:

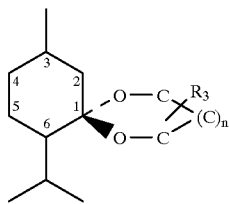

wherein $R_3$ is a member of the group consisting of a hydroxy, lower alkoxy, and lower alkyl, and n is an integer of 0 or 1.

5. The method of claim 1 or 2, wherein the flavor ingredients comprise menthone ketal at a level of about 0.1% to about 50% by weight of the flavor ingredients.

6. A low moisture food, pharmaceutical or other oral composition which comprise flavor ingredients, said flavor ingredients comprising a menthone ketal.

7. An oral composition having enhanced flavor, said oral composition selected from the group consisting of food, pharmaceutical, toothpaste, and mouthwash and comprising about 0.001% to about 2% flavor ingredients, said flavor ingredients comprising a menthone ketal.

8. The oral composition of claim 6 or 7, wherein said menthone ketal is a compound of the formula:

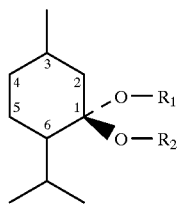

wherein $R_1$ and $R_2$ are alkyl groups.

9. The oral composition of claim 6 or 7, wherein said menthone ketal is a compound of the formula:

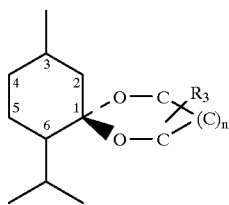

wherein $R_3$ is a member of the group consisting of a hydroxy, lower alkoxy, and lower alkyl, and n is an integer of 0 or 1.

10. The oral composition of claim 9, wherein $R_3$ is 5'-hydroxy and n is 1.

11. The oral composition of claim 9, wherein $R_3$ is selected from the group consisting of methoxy or methyl, and n is 0.

12. The oral composition of claim 11, wherein $R_3$ is 5'-methoxy.

13. The oral composition of claim 11, wherein $R_3$ is 4'-methoxy.

14. The oral composition of claim 11, wherein $R_3$ is 4'-methyl.

15. The oral composition of claim 11, wherein $R_3$ is 5'-methyl.

16. The oral composition of claim 6 wherein the flavor ingredients comprise about 0.001% to about 2% of said oral composition.

17. The oral composition of claim 16, wherein menthone ketal is present at a level of about 0.1% to about 50% by weight of the flavor ingredients.

18. The oral composition of claim 6, wherein said composition is a toothpaste.

19. The oral composition of claim 6, wherein said composition is a mouthwash.

20. The composition of claim 7 wherein said menthone ketal is present at a level of about 0.1% to about 50% by weight of the flavor ingredients.

21. A method of achieving a cooling effect on human mucous membrane which comprises applying to such mucous membrane an effective amount of a composition comprising at least one ketal of the formula

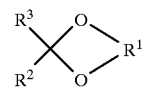

in which $R^1$ represents a $C_2$–$C_6$-alkylene radical having at least 1, but not more than 3, hydroxyl group(s), and $R^2$ and $R^3$ together represent an alkylene radical which, together with the carbon atom which carries the radicals $R^2$ and $R^3$, forms a 6 membered ring, said alkylene radical being substituted by a methyl radical in a position meta to the carbon which carries the radicals $R^2$ and $R^3$ and an isopropyl radical in the position para to the methyl radical.

22. The method according to claim 21, where $R^1$ denotes a 1,2- or 1,3-alkylene radical.

23. The method according to claim 21, where $R^1$ denotes

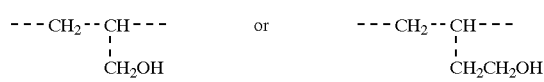

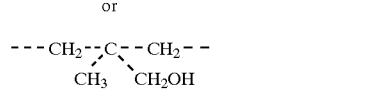

* * * * *

UNITED STATES PATENT AND TRADEMARK OFFICE
CERTIFICATE OF CORRECTION

PATENT NO. : 5,977,166
DATED : November 2, 1999
INVENTOR(S) : Michael J. Greenberg It is certified that error appears in the above-identified patent and that said Letters Patent is hereby corrected as shown below:

In claim 7, line 3, delete "comprisina" and substitute --comprising-- in its place.

Signed and Sealed this

Twenty-second Day of May, 2001

Attest:

NICHOLAS P. GODICI

Attesting Officer   Acting Director of the United States Patent and Trademark Office